(12) United States Patent
Högfors et al.

(10) Patent No.: US 6,450,027 B1
(45) Date of Patent: Sep. 17, 2002

(54) DEVICE FOR DETERMINING A STRENGTH PROFILE OF A HUMAN LIMB

(76) Inventors: Christian Högfors, Box 156, 524 22 Herrljunga (SE); Mohsen Makhsous, 215 East Chicago Ave. #1903, Chicago, IL (US) 60611; Fang Lin, 244 East Pearson Rd. #802, Chicago, IL (US) 60611

( * ) Notice: Subject to any disclaimer, the term of this patent is extended or adjusted under 35 U.S.C. 154(b) by 0 days.

(21) Appl. No.: 09/648,266

(22) Filed: Aug. 25, 2000

(51) Int. Cl.[7] ................................. A61B 5/22
(52) U.S. Cl. .................... 73/379.01; 73/862.045; 600/587
(58) Field of Search ............ 73/862.041, 862.042, 73/862.043, 862.044, 862.045, 862.046, 379.1; 600/587

(56) References Cited

U.S. PATENT DOCUMENTS 4,046,262 A * 9/1977 Vykukal et al. .......... 214/1 CM
5,490,427 A * 2/1996 Yee et al. .................... 73/767
6,038,933 A * 3/2000 Meyer ................... 73/862.045

* cited by examiner

*Primary Examiner*—Max Noori
(74) *Attorney, Agent, or Firm*—Samuels, Gauthier & Stevens, LLP

(57) ABSTRACT

A device for determining a strength profile of a human limb. The device comprises a first tubular member and a support intended to be suspended in a fixed position in relation to a coordinate system X-, y and z-axes. The first tubular member is arranged for holding the human limb and for being in contact with the support via at least one force sensor arranged for detecting forces exercised by the human limb on the first tubular member in directions in the coordinate system when determining the strength profile, wherein the coordinate system is three-dimension and has x-, y and z-axes and the force sensor is/are arranged for detecting forces along each of the x-, y and z-axes. The determined strength profile, for e.g. an arm or a leg of a human subject, can be presented as a table or diagram illustrating the forces and torques the human limb in question can exercise in different directions in the coordinate system. The device according to the invention is a useful tool in ergonomic, orthopaedic and research work.

5 Claims, 3 Drawing Sheets

DEVICE FOR DETERMINING A STRENGTH PROFILE OF A HUMAN LIMB

TECHNICAL FIELD

The present invention relates to a device for determining a strength profile of a human limb. The device according to the invention enables the determination of a strength profile, for e.g. an arm or a leg of a human subject. The strength profile can be presented as a table or diagram illustrating the forces and torques the human limb in question can exercise in different directions in a suitable coordinate system. The device according to the invention is a useful tool in ergonomic, orthopaedic and research work.

BACKGROUND OF THE INVENTION

It is previously known with a number of different devices which can determine the strength profile of a human limb.

Accordingly, in an study published in *Journal of Neurophysiology*, Vol. 62, NO. 6, December 1989, Buchanan et al. disclose force measurements using a 3 degrees-of-freedom load cell for measuring the force at the wrist of a human subject. The disclosed device consisted of six pairs of strain gauges which decomposed forces into flexion-extension, up-down (or varus-valgus), and supination-pronation components. The disclosed device enabled different muscles to be examined in eight torque directions. During the experiments, the subject was seated with his arm in the load apparatus, watching a target on a monitor. As each target appeared on the monitor, the subject was to manipulate a cursor, by means of exercising a force on the load apparatus with his/her arm, to be within target boundaries on the screen and to maintain the cursor in this position for 2,5 seconds.

Furthermore, in a Thesis in partial fulfilment of the degree of Licentiate of Engineering, Paper II, Chalmers University of Technology, Gothenburg 1996, Makhsous et. al. disclose the determination of strength profiles using a force device which consists of two short tubes of stainless steel connected to each other by four smaller tubes of spring steel with longitudinal slits. These small tubes are resilient enough to allow the measurement of the deformation caused by translating the inner tube relative to the outer tube in radial direction. In order to measure the deformation in the small tubes, two strain gauges are bonded to the inner and outer surfaces of each tube, so that both compression and elongation on both sides of the tube walls can be detected.

However, the previously known devices for determining a strength profile of a human limb do not provide the possibility to determine forces and torques in all three dimensions in a three-dimensional coordinate system.

Furthermore, some of the previously known devices have a complicated design and function, and can accidentally be broken or disturbed by a human subject.

SUMMARY OF THE INVENTION

Accordingly, the first object of the present invention is to provide a simple, inexpensive, reliable and robust device for determining a strength profile of a human limb, which device is able to determine forces in any direction, and preferably also torques around axes extending in any direction, in a three-dimensional coordinate system.

In accordance with claim 1, this first object is achieved by means of a device comprising a first tubular member and a supporting means intended to be suspended in a fixed position in relation to a coordinate system. The first tubular member is arranged for holding the human limb and for being in contact with the supporting means via at least one force sensor means arranged for detecting forces exercised by the human limb on the first tubular member in directions in the coordinate system when determining the strength profile. Thereby, the coordinate system in three-dimensional and has x-, y and z-axes and the force sensor means is/are arranged for detecting forces along each of the x-, y- and z-axes.

Further objects of the present invention will become evident from the following description, and the features enabling these further objects to be achieved are listed in the dependent claims.

BRIEF DESCRIPTION OF THE DRAWINGS

In the following, the present invention will be described in greater detail with reference to the attached drawings, in which.

DETAILED DESCRIPTION OF PREFERRED EMBODIMENTS

In the following, a preferred embodiment of the device according to the invention will be described with reference to the attached FIGS. 1–4.

The device 101; 201 is intended for determining a strength profile of a human limb. Such strength profiles can be presented in different ways, e.g. in form of tables or diagrams, and are useful in connection with ergonomic, orthopaedic and research work.

Figure 1:
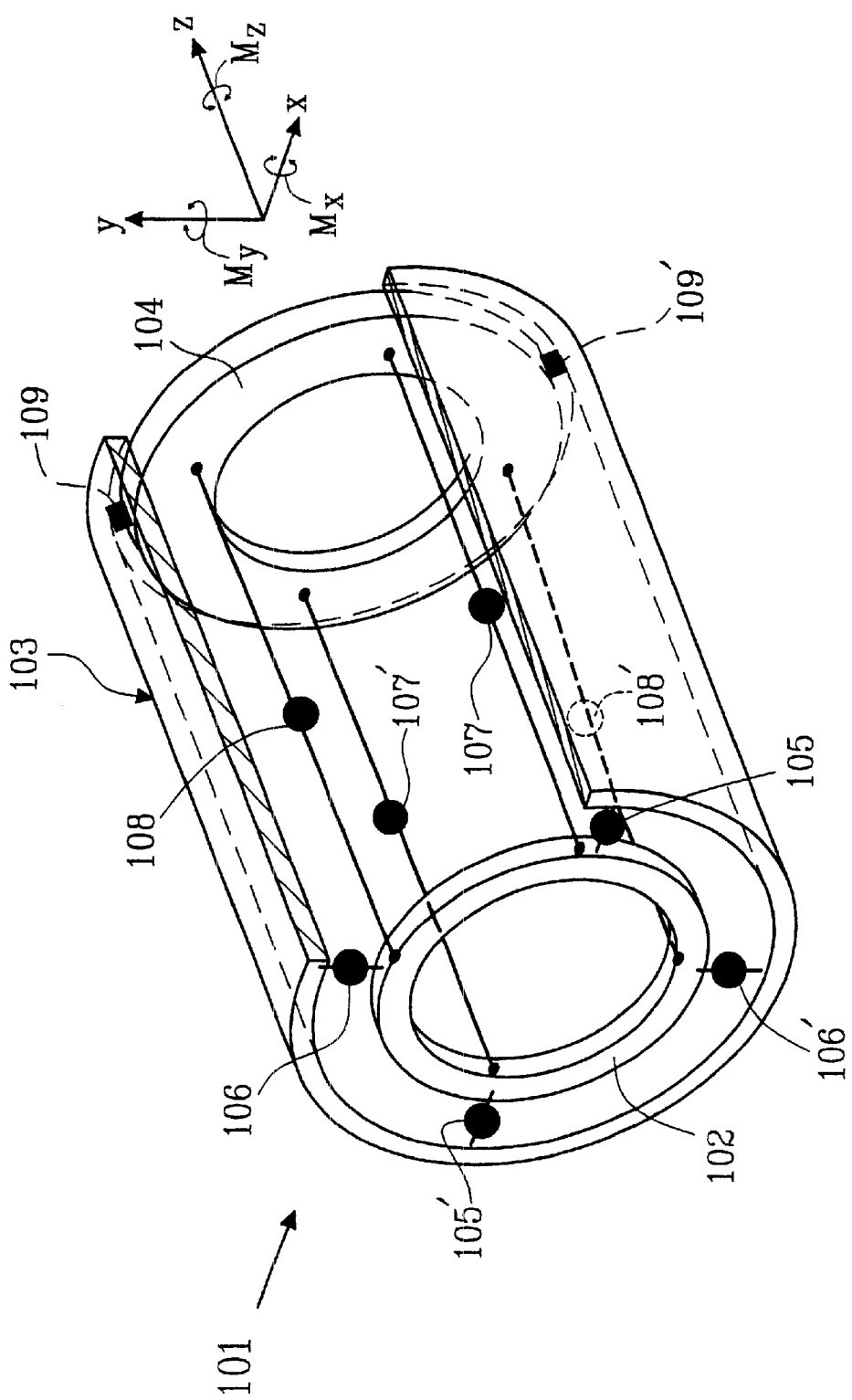
FIG. 1 shows a schematic perspective view of a device according to the invention, with a cut-away portion.
Figure 2A:
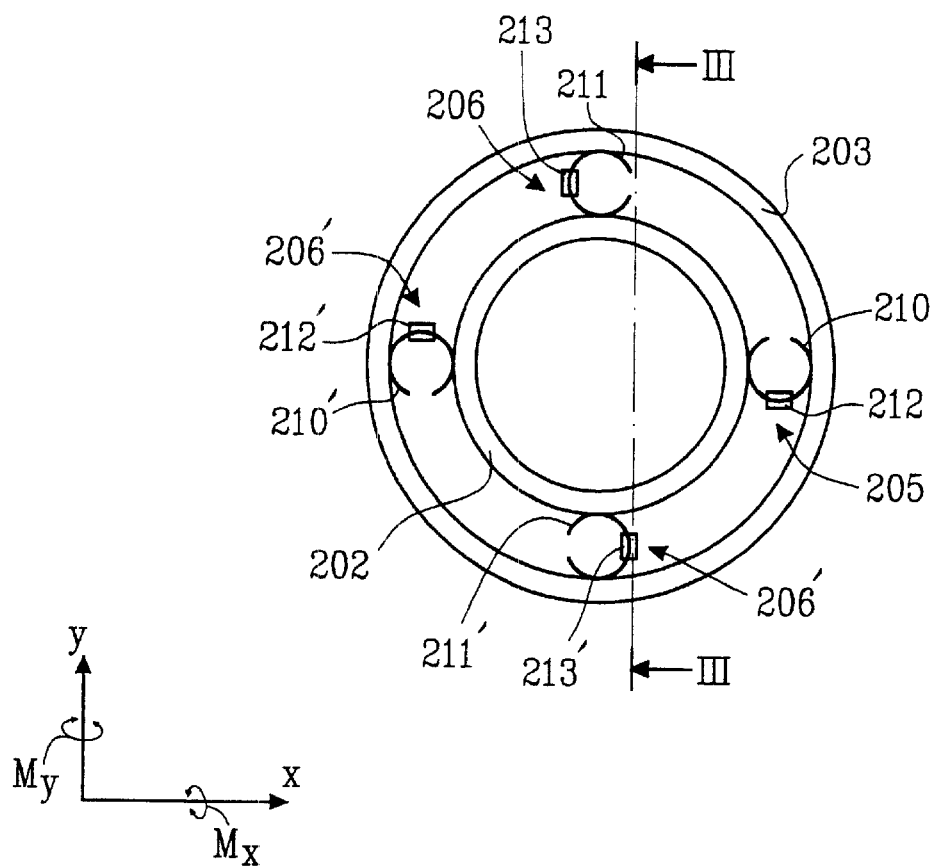
FIG. 2A shows a schematic view of a device according to a preferred embodiment of the invention, seen from the end of the device where a human limb is to be inserted.
Figure 3:
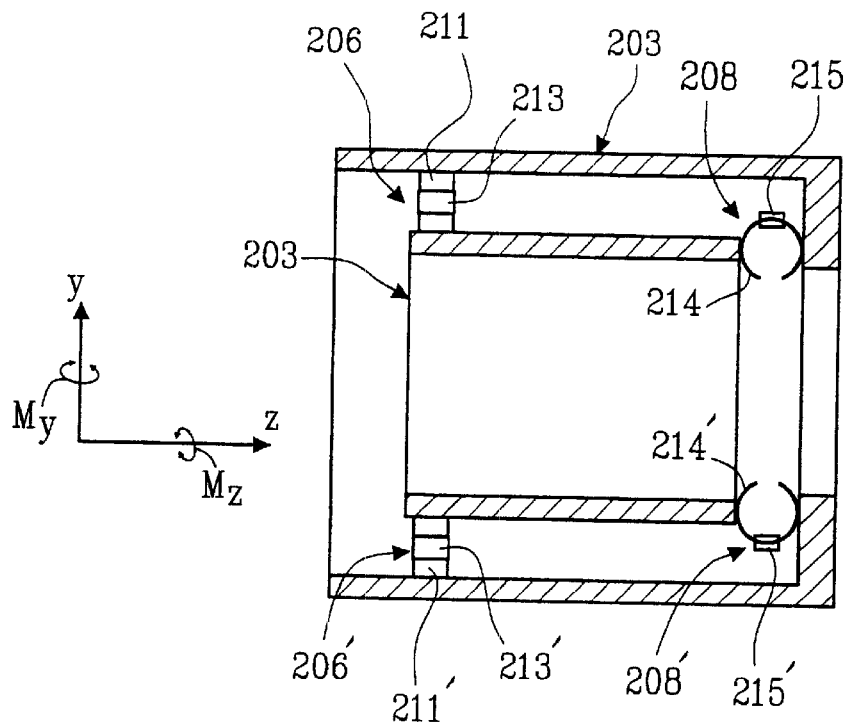
FIG. 3 shows a schematic perspective view of a force sensor means intended to be included in a device according to an alternative embodiment of the invention.

The device comprises a first tubular member 102; 202; 302 and a supporting means 103, 104; 203; 303 which is intended to be suspended in a fixed position in relation to a coordinate system, as shown in FIGS. 1, 2A and 3. The suspension of the supporting means in the fixed position can be accomplished in any suitable way, e.g. by means of a suitable rack (not shown in the drawings) fixed to the floor or to another suitable foundation (not shown), or by means of a beam (not shown) attached to a wall or a ceiling.

In the device according to the invention, the above-mentioned first tubular member 102; 202; 302 is arranged for holding the human limb for which a strength profile is to be determined. Thereby, the human limb is preferably an arm or a leg of a human subject whose strength profile is to be determined. However, it must be understood that the expression "human limb", as used herein, refers to the fact that the limb in question contacts the device according to the invention during the determination. The skilled person will understand that a number of different strength profiles can be determined by means of the device according to the invention. If, for example, the first tubular member 102; 202; 302 holds the hand of a human subject during the determination, the result will be a strength profile corresponding to the status of the forearm muscles. If the first tubular member instead holds the forearm of the subject during the determination, the strength profile can correspond to the status of the upper arm muscles (and possibly the shoulder muscles). If the first tubular member holds the upper arm during the determination, the strength profile can correspond to the status of the shoulder muscles. In an analogous way, by means of allowing the first tubular member to hold the foot, lower leg and thigh, respectively, strength profiles corresponding to the status of the muscles in the lower leg, the thigh and hip area can be determined. Furthermore, different motion patterns of the subject in question will activate different muscles and, consequently, decide the actual strength profile which is determined.

The first tubular member 102; 202; 302 is also arranged for being in contact with the supporting means 104; 203; 303 via a plurality of force sensor means 105, 105', 106, 106', 107, 107', 108, 108'; 205, 205', 206, 206', 208, 208'; 305 which is/are arranged for detecting forces exercised by the human limb on the first tubular member 102; 202; 302 in directions in the coordinate system when determining the strength profile.

According to the invention, the coordinate system in three-dimensional and has x-, y-and z-axes. Thereby, the force sensor means is/are arranged for detecting forces along each of the x- 105, 105'; 205, 205', y- 106, 106'; 206, 206' and z-axes 107, 107', 108, 108'; 208, 208'.

In preferred embodiment of the invention, several of the force sensor means are arranged opposite each other in pairs 105; 205 and 105'; 205', 106; 206 and 106'; 206', 107 and 107', 108; 208 and 108'; 208' in contact with the first tubular member 102; 202. Thereby, the force sensor means are arranged for emitting force signals which also enable torques Mx, My, Mz around axes extending in any direction in said three-dimensional coordinate system to be calculated from the difference in force signal between force sensor means in different pairs.

In a particularly preferred embodiment of the device according to the invention, the above-mentioned torque determination is accomplished by means of at least one of the force sensor means 205, 205', 206, 206', 208, 208' comprising a split annular member 210, 210', 211, 211', 214, 214' firmly attached to the first tubular member 202 and to the supporting means 203, 204. Thereby, at least one strain gauge 212, 212', 213, 213', 215, 215' is arranged in contact with both the inner and outer surface of the split annular member, so that the strain gauge 212, 212', 213, 213', 215, 215' can detect both a force striving to expand the split annular member and a force striving to compress the split annular member. However, also embodiments with other configurations of the force sensor means enabling torque determination are conceivable.

Figure 2B:
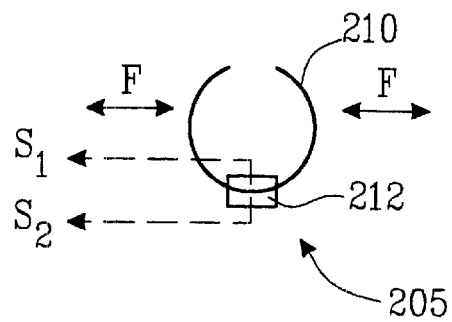
FIG. 2B illustrates the function of a force sensor means included in the device in FIG. 2A.

In one advantageous embodiment of the device according to the invention, particularly illustrated in FIG. 2B, the contact of the strain gauge 212 with the inner surface of the split annular member 210 produces a first signal S1 and the contact with the outer surface of the split annular member produces a second signal S2 when the tubular member is subjected to the expanding or compressing force (F). Thereby, the difference ΔS=S2−S1 between the second and first signal is intended to be used as an output signal from the force sensor means 205. This advantageous embodiment reduces the need for calibration of the force sensor means 205, since the relative difference ΔS between the second signal S2 and the first signal S1 can be used for the determination of the strength profile without any need for "taring" the force sensor means 205 to a "zero level".

In another advantageous embodiment of the device according to the invention, the supporting means comprises a second tubular member 104 which is firmly attached to the inner surface of a housing 103 by means of attachment means 109, 109'. Thereby, the force sensor means 105, 105', 106, 106', 107, 107', 108, 108' are arranged in contact with the second tubular member 104. In this embodiment, the device according to the invention will be particularly easy to manufacture and assemble. The above-mentioned attachment means can be e.g. a weld, a screw fastening or any other suitable rigid attachment between the second tubular member 104 and the housing 103. However, it is also conceivable with embodiments of the invention in which the supporting means 203 e.g. consists of a single hollow body with a cylindrical internal cavity.

Particularly advantageously, the signals from the force sensor means 105, 105', 106, 106', 107, 107', 108, 108'; 205, 205', 206, 206', 208, 208'; 305 are conducted via signal lines (not shown) to a computer (not shown) in which the signals by means of a microprocessor (not shown) and a suitable software are translated into the strength profile (not shown) which can be viewed in the form of a table or a diagram on a monitor (not shown), a computer printout (not shown), or the like.

The present invention should by no means be regarded as being limited to the above-described embodiments, or to what is shown in the attached drawings, but the scope of the invention is defined in the following claims.

Figure 4:
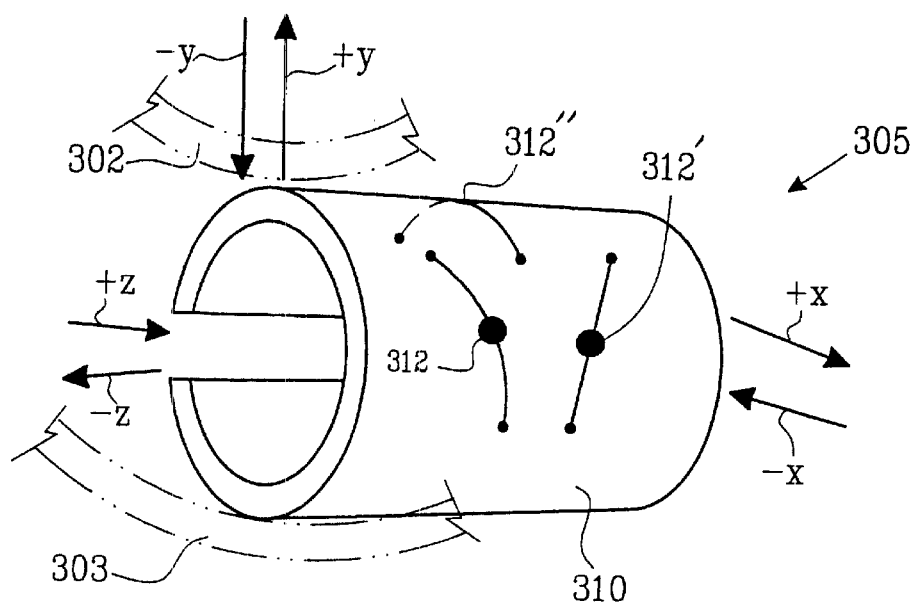

Accordingly, in an alternative embodiment of the device according to the invention illustrated in FIG. 4, at least one of the force sensor means 305 comprises a split annular member 310 firmly attached to the first tubular member and to the supporting means. In this embodiment, a first strain gauge 312 is arranged in contact with a first surface portion of the split annular member 310 along a first line while a second strain gauge 312' is arranged in contact with a second surface portion of the split annular member 310 along a second line. Thereby, the first line is arranged at an angle in relation to the first line. This enables the strain gauges 312, 312' to detect both forces striving to split +y or compress −y the split annular member 310 and forces striving to shear +z, −z the split annular member axially. Accordingly, this embodiment reduces the number of force sensor means needed in the device according to the invention.

In another alternative embodiment, also illustrated in FIG. 4, a third strain gauge 312" is arranged in contact with a third surface portion of the split annular member 310 along a third line. In this embodiment, the third line is arranged at an angle in relation to the first and second lines so that the strain gauges 312, 312', 312" of one single force sensor means 305 can detect forces along each of said x-, y- and z-axes. Accordingly, in this embodiment only one single sensor means 305 in contact with the first tubular member 302 and the supporting means 302 is needed in the device according to the invention. Hereby it is possible to facilitate a calculation of all forces in all directions, as well as the axial moment.

What is claimed is:

1. A method for determining the strength of a human limb, said method comprising:

placing a limb in a device, the device includes a first tubular member and supporting means intended to be suspended in a fixed position in relation to a coordinate system, the first tubular member is for holding a human limb and is in contact with support means via at least one force sensor means;

detecting forces exercised by the human limb on the first tubular member in directions in the coordinate system when determining said strength profile, such that the coordinate system is three-dimensional and has x-, y and z-axes;

detecting forces with the force sensor means along each of said x-, y and z-axes;

emitting force signals from the force sensor means which are arranged to enable torques (Mx, My, Mz) around axes extending in any direction in the three-dimensional coordinate system; and calculating the difference in force signal between force sensor means in different pairs to determine the strength profile of the human limb.

2. The method of claim 1, wherein several of said force sensor means are arranged opposite each other in several pairs in contact with said first tubular member.

3. The method of claim 1, wherein the device includes a split annular member having an inner and an outer surface and at least one strain gauge, such that said method further comprises detecting both a force striving to expand the split annular member and a force striving to compress the split annular member.

4. The method of claim 1, further including conducting signals from the force sensor means via signal lines to a computer; and a translating the signals by means of a microprocessor and suitable software into a strength profile which can be viewed in the form of a table, or a diagram on a monitor, a computer printout, or the like.

5. The method according to claim 1, wherein at least one of said force sensor means comprises a split annular member firmly attached to said first tubular member and to said supporting means, and wherein a first strain gauge is arranged in contact with a first surface portion of said split annular member along a first line and a second strain gauge is arranged in contact with a second surface portion of said split annular member along a second line, said first line being angled at an angle in relation to said first line, and wherein the method further includes detecting both forces with the strain gauges arriving to split (+y) or compress (−y).

* * * * *